United States Patent [19]

Globus

[11] Patent Number: 4,954,316

[45] Date of Patent: Sep. 4, 1990

[54] STABLE, ACTIVE CHLORINE CONTAINING ANTI-MICROBIAL COMPOSITIONS

[76] Inventor: Alfred R. Globus, 26-53 210th St., Bayside, N.Y. 11365

[21] Appl. No.: 288,241

[22] Filed: Dec. 22, 1988

Related U.S. Application Data

[63] Continuation-in-part of Ser. No. 116,203, Oct. 3, 1987, abandoned.

[51] Int. Cl.$^5$ ............................................. A61L 218/00
[52] U.S. Cl. ......................................... 422/37; 422/29; 424/405; 424/409; 514/245
[58] Field of Search ...................... 252/186.35, 187.34, 252/89.1, 102, 106, 99, 174.13; 514/241, 245, 519; 422/29, 37; 424/405, 409

[56] References Cited

U.S. PATENT DOCUMENTS

| | | | |
|---|---|---|---|
| 3,346,612 | 10/1967 | Hansen | 260/456 |
| 3,390,092 | 6/1968 | Keast | 252/99 |
| 3,868,336 | 2/1975 | Mazzola et al. | 252/527 |
| 4,089,804 | 5/1978 | Falk | 252/355 |
| 4,171,282 | 10/1979 | Mueller | 252/356 |
| 4,287,080 | 9/1981 | Siklosi | 252/104 |
| 4,409,117 | 10/1983 | Holmberg et al. | 252/186.35 X |
| 4,443,364 | 4/1984 | Klinger et al. | 252/547 |
| 4,822,512 | 4/1989 | Auchincloss | 252/187.21 X |

OTHER PUBLICATIONS

Fluorad ® Fluorochemical Surfactant, Technical Information, Commercial Chemicals Div. 3M Company, 3M Center, St. Paul, Minn. 55101.
Monflor ® Publication, "Introducing Unique New Monflor ® Fluorochemical Surface Active Agents", Monflor ®–Imperial Chemical Industries Ltd.

Primary Examiner—Matthew A. Thexton
Assistant Examiner—Joseph D. Anthony
Attorney, Agent, or Firm—Evelyn M. Sommer

[57] ABSTRACT

Anti-microbial compositions in the form of dry powders substantially instantly soluble in water, which exhibit stability for prolonged periods of time even at elevated temperatures of up to 130° F., obtained by admixing an organic surfactant in which substantially all of the available oxidable groups have been replaced with fluorine to form a perfluoro surfactant, with a chlorinated isocyanuric acid. Preferably the anti-microbial compositions are obtained by admixing the following: trichloroisocyanuric acid, potassium hydroxide in an amount sufficient to neutralize the trichloroisocyanuric acid to its potassium salt, a fluorinated anionic surfactant, potassium monohydrogen phosphate and potassium chloride.

11 Claims, No Drawings

STABLE, ACTIVE CHLORINE CONTAINING ANTI-MICROBIAL COMPOSITIONS

This application is a continuation-in-part of application Ser. No. 116,203 filed Oct. 3, 1987 now abandoned.

This invention relates to active chlorine containing anti-microbial compositions. In particular this invention is concerned with dry, powder form active chlorine containing anti-microbial compositions which are highly soluble in water and their application to disinfecting and/or sterilizing operations.

The use of dry powders containing active available chlorine which is released as hypochlorous acid upon hydrolysis as disinfecting or sanitizing agents is well known. It is also known to employ for this purpose chlorinated cyanuric acids per se or in the form of their salts as disinfecting and/or sterilizing agents, for example, in the maintenance of swimming pools. However, while these compounds are stable in themselves, they do not exhibit the necessary surfactancy to make them effective wetting and penetrating agents.

Thus, despite their many advantages disinfecting and/or sterilizing agents of the active chlorine releasing type and in particular the chlorinated cyanuric acids are as a class, not optimally effective.

In an effort to realize the full potential of the active chlorine releasing type sterilizing agents, such materials have been the focus of considerable research and development effort over the years. One result of these investigations was the finding that combining an organic surfactant, preferably a water soluble surfactant with the active chlorine releasing compound amplified the sterilizing power of the resulting active chlorine releasing compound. However, the combination of a powerful chlorinating agent with the water soluble surfactant brings about a slow reaction in which the surfactant is oxidized with the formation of water which increases the release of hypochlorous acid in the container resulting in a slow destruction, i.e., degradation of the active component, which degradation is accelerated at elevated temperatures. In an effort to avoid this loss of activity, i.e., decomposition of the dry mixture of the active chlorine containing compound and organic surfactant, it has been proposed that the compositions be maintained under refrigeration. This, as can be appreciated, is not always practical, as for example, when the compositions are required to be used under emergency conditions, as by the armed forces or disaster personnel under field conditions or in underdeveloped countries where refrigeration may not be available.

The active chlorine groups of the aforesaid compositions are also subject to hydrolytic cleavage since loss of sterilizing power is activated under conditions of high humidity.

It is an object of this invention to provide active chlorine containing compositions useful for sterilizing and/or disinfecting and more particularly, as anti-microbials and to provide means for substantially decreasing their decomposition.

It is another object of the invention to provide such compositions in dry powder form comprising an especially prepared mixture of a powerful chlorinating agent with a water-soluble organic surfactant.

It is a further object of the invention to provide such compositions in dry powder form comprising a mixture of a powerful chlorinating agent having from about 50 to 90% available chlorine with a water soluble organic surfactant, which compositions are stable on storage including at elevated temperatures of up to about 130° F.

It is yet a further object of the invention to provide such compositions in dry powder form which are instantly soluble in water.

Still another object of the invention is to provide such compositions in dry powder form stable on storage including at elevated temperatures of up to about 130° F., which are instantly soluble in water which comprise a mixture of a trichloroisocyanuric acid or a salt thereof with an organic water soluble non-toxic surfactant The applicant has now discovered that the decomposition of the active chlorine containing compound leading to loss of available chlorine in the antimicrobial composition is avoided by the present invention which stabilizes the decomposition rate of the active chlorine containing compound by the addition of a particular surfactant and diluent.

According to the present invention, anti-microbial compositions in the form of dry powders substantially instantly soluble in water, which exhibit stability for prolonged periods of time even at elevated temperatures of up to 130° F. are obtained by admixing an organic surfactant in which all or substantially all of the available oxidizable groups have been replaced with fluorine to form a perfluoro surfactant with a chlorinated isocyanuric acid.

More particularly, the invention is directed to antimicrobial compositions having the aforedescribed properties which are obtained by admixing as will be hereinafter described, the following:

1. trichloroisocyanuric acid (90% available chlorine)
2. potassium hydroxide in an amount sufficient to neutralize the trichloroisocyanuric acid to the potassium salt
3. a fluorinated anionic surfactant
4. potassium monohydrogen phosphate
5. potassium chloride It is also within the scope of the invention to employ the trichlorisocyanuric acid already in the form of its salt and specifically as its potassium salt.

The presence of the fluorinated surfactant is required if stability, i.e., loss of available chlorine is to be controlled or eliminated. This can be observed if the mixture is prepared using an organic surfactant in which less than all of the oxidizable hydrogen groups have been replaced with fluorine. As the fluorine replacement in the surfactant is increased, the decomposition rate of the active chlorine containing compound is decreased, thus increasing the amount of available chlorine for enhanced sterilizing and/or disinfecting performance.

Generally speaking, the fluorinated organic surfactants constitute a known class of chemical entities, representative members of which are disclosed in the technical literature. They can be prepared by treating the surfactant with fluorine until all or substantially the entirety of the available hydrogen groups have been replaced with fluorine. The Applicant does not claim the method of preparing these fluorinated organic surfactants. Rather his invention lies in the finding, first, that by the use of a fluorinated organic surfactant, the available chlorine in the active chlorine containing compound is unable to act upon the fluorinated organic surfactant thus forming a stable composition. Second, it has been found in accordance with the invention, that by substituting the hydrogen groups with fluorine, the effectiveness of the resulting surfactant is markedly increased as to its wetting, penetrating and emulsifying properties as compared to the starting material. This has the attendant advantage of offsetting any increase in costs associated with the preparation of the fluorinated compounds.

The applicant has found that when using 0.1 to 2.0% and preferably 0.1% to 1% and most preferably 0.5% of the fluorinated surfactant, the same wetting properties are realized as when 10% of the corresponding unfluorinated compound is used.

The applicant has found that when the compositions are formulated using 0.5% of the fluorinated surfactant, the compositions withstand exposure to temperatures of 165° F. for periods of one week. If on the other hand, the compositions are formulated using concentrations exceeding 2% of the fluorinated surfactant, the stability falls off rapidly, such lack of stability occuring already at lower temperatures.

Suitable active chlorine containing compounds in accordance with the invention are derivatives of trichloroisocyanuric acid or salts thereof, preferably 1,3,5-trichloro-5-triazine-2,4,6-trione or its salts, i.e., alkali metal salts and preferably its sodium, potassium or lithium salt, most preferably the sodium or potassium salt. The most preferred salt is the potassium salt of trichloroisocyanuric acid. In preparing the compositions of the invention, it is possible to employ the trichlorisocyanuric acid per se and to form the potassium salt by introduction of sufficient potassium hydroxide to substantially completely convert the acid to the salt or alternatively to use in formulating the composition, the potassium salt of trichloroisocyanuric acid.

The aforesaid active chlorine containing compounds contain very high percentages of active available chlorine There are in the United States certain laws which require that products which contain high percentages of active chlorine, i.e., amounts in excess of 10%, be labelled with the term "POISON." For that reason, i.e., to avoid such labeling problems, the compositions of the invention are diluted with a water soluble salt such as an alkali metal or alkaline earth metal chloride or sulfate The choice of salt is controlled in that it must be one which is not reactable with chlorine. Sodium chloride, potassium chloride, sodium sulfate and potassium sulfate are preferred salts for this purpose, potassium chloride being most preferred. The use of potassium chloride as the salt is as already noted most preferred It serves not only as a diluent but as a carrier for the potassium monohydrogen phosphate. It is critical to the invention that the composition of the invention exist in the form of a free flowing powder and that when used it be readily and substantially immediately soluble in water. It is the presence of the potassium chloride which imparts the desired solubility to the composition, i.e., the final composition when introduced into water enters solution instantly. In all instances, solubilization takes place in up to six (6) seconds.

Because of the hygroscopic properties of potassium chloride, the applicant has found that if the potassium chloride is ground in an apparatus which exerts a smashing effect on the particles of potassium chloride, as for example a hammer mill, and if the grinding is carried out so as to produce particles of potassium chloride the preponderance of which have a mesh size of about -100to + 325, most preferably in the 200 mesh range, the desired properties are obtained It is critical that the particles not be ground to a range finer than indicated as then the particles will assume hygroscopic properties and also that they not be coarser than indicated as then separation, i.e., stratification occurs, again with the fines being undesirably hygroscopic.

The grinding should not be carried out in a ball mill as it has been found that such grinding results in the formation of a solid cake material entirely unsuitable for use in formulating the compositions of the invention.

After the potassium chloride has been ground as afore-described, the potassium chloride is introduced into a rotating drum type mixer with the potassium monohydrogen phosphate (anhydrous). In this regard, while it is preferred to use the monohydrogen phosphate, it is also possible to use a mixture of potassium phosphate ($K_3PO_4$) and potassium dihydrogen phosphate ($KH_2PO_4$) producing the potassium monohydrogen phosphate ($K_2HPO_4$) in situ. In the rotating drum, the fine particles of potassium chloride are coated with the phosphate thereby preventing the potassium chloride from picking up moisture, i.e., premature solubilization of the potassium chloride and interference with the free flowing powder properties necessary for satisfactory application of the composition. The phosphate coated potassium chloride is easily soluble in water and is extremely well suited for use in the process of the invention.

The trichloroisocyanuric acid as its potassium salt and the fluorinated anionic surfactant are then introduced to form the composition of the invention.

The concentration of the active chlorine containing compound in the composition preferably is such as to provide a final available chlorine content which does not exceed 9.9%

The concentration of the fluorinated surfactant in the antimicrobial composition depends to a large extent on the concentration of the active chlorine containing compound which in turn depends on the particular use for which a given composition is formulated. Higher or lower levels can be selected according to the needs of the formulator. Overall, increased sterilizing and/or disinfecting results are realized when the active chlorine containing compound and the fluorinated organic surfactant are present in a ratio in the range of from about 50:1 to 10:1 (parts by weight) and preferably from about 40:1 to 20:1 (trichloroisocyanuric acid: fluorinated surfactant).

In preparing the compositions of the invention, the fluorinated surfactant is introduced into the drum which contains the monohydrogen phosphate coated potassium chloride particles and trichloroisocyanuric acid salt for admixture therewith.

Since an aqueous solution of per acids or per salts is generally acidic, it is preferable to maintain the requisite pH conditions so that, in aqueous solution, a pH of about 6 to 8 and preferably 7.5 to 7.8 is realized. This is accomplished by means of the potassium mono hydrogen phosphate.

The potassium mono hydrogen phosphate utilized in formulating the compositions of the invention serves as more than a buffer. It has a pH of 9.2 and yet provides a pH in the desired range (5.0 to 8.0) when used in association with the other components of the composition in the form of a solution thereof. In addition, the potassium mono hydrogen phosphate serves as a stabilizer for the composition in both its dry and wet forms.

The potassium monohydrogen phosphate acts so as to isolate the potassium chloride from ambient and other moisture and thereby helps to maintain the product free flowing and to prevent premature liquefaction of the potassium chloride which would interfere with the latter's solubilization properties.

The potassium mono hydrogen phosphate also possesses the property of an extremely low toxicity.

As noted above, the potassium chloride is present in an amount required to maintain the 10% available chlorine limitation. If the limitation is not required, the formulation may be adjusted to provide a higher available chlorine content.

Organic surfactants which when fluorinated are suitable for incorporation into the compositions of the invention encompass a relatively wide range of materials of the anionic type. The most important criteria in the selection of the fluorinated surfactant is that it have a very low toxicity. The $LD_{50}$*as determined by conventional methods in the rat should preferably amount to about 5 gm/kg and the $LD_{50}$ should not be less than 2 gm/kg as measured in the rat.
*Lethal dose for 50% of the test animals The anionic surface active agents include those surface active or detergent compounds which contain an organic hydrophobic group as an anionic solubilizing group. Typical examples of anionic solubilizing groups are sulfonate, sulfate, carboxylate, phosphonate and phosphate. Examples of suitable anionic detergents which fall within the scope of the invention include the soaps, such as the water-soluble salts of higher fatty acids or rosin acids, such as may be derived from fats, oils and waxes of animals, vegetable or marine origin, for example, the sodium soaps of tallow, grease, coconut oil, tall oil and mixtures thereof; and the sulfated and sulfonated synthetic detergents, particularly those having about 8 to 26, and preferably about 12 to 22, Carbon atoms to the molecule.

As examples of suitable synthetic anionic detergents the higher alkyl mononuclear aromatic sulfonates are preferred, particularly the LAS type such as the higher alkyl benzene sulfonates containing from 10 to 16 carbon atoms in the alkyl group, for example, the sodium salts such as decyl, undecyl, dodecyl (lauryl), tridecyl, tetradecyl, pentadecyl, or hexadecyl benzene sulfonate and the higher alkyl toluene, xylene and phenol sulfonates; alkyl naphthalene sulfonate, ammonium diamyl naphthalene sulfonate, and sodium dinonyl naphthalene sulfonate.

Other anionic detergents are the olefin sulfonates including long chain alkene sulfonates, long chain hydroxyalkane sulfonates or mixtures of alkenesulfonates and hydroxyalkanesulfonates. These olefin sulfonate detergents may be prepared, in known manner, by the reaction of $SO_3$ with long chain olefins (of 8-25 preferably 12-21 carbon atoms) of the formula $RCH-CHR^1$, where R is an alkyl and $R^1$ is alkyl or hydrogen, to produce a mixture of sulfones and alkenesulfonic acids, which mixture is then treated to convert the sulfones and sulfonates. Examples of other sulfate or sulfonate detergents are paraffin sulfonates, such as the reaction products of alpha olefins and bisulfites (for example, sodium bisulfite), for example, primary paraffin sulfonates of about 10-20 preferably about 15-20 carbon atoms; sulfates of higher alcohols; salts of α-sulfofatty esters for example of about 10 to 20 carbon atoms, such as methyl α-sulfomyristate or α-sulfotallowate.

Examples of sulfates of higher alcohols are sodium lauryl sulfate, sodium tallow alcohol sulfate; Turkey Red Oil or other sulfated oils, or sulfates of mono- or diglycerides of fatty acids (for example, stearic monoglyceride monosulfate), alkyl poly(ethenoxy)ether sulfates such as the sulfates of the condensation products of ethylene oxide and lauryl alcohol (usually having 1 to 5 ethenoxy groups per molecule); lauryl and other higher alkyl glyceryl ether sulfonates; aromatic poly(ethenoxy)ether sulfates such as the sulfates of the condensation products of ethylene oxide and nonyl phenol (usually having 1 to 20 oxyethylene groups per molecule, preferably 2-12).

The suitable anionic detergents include also the acyl sarcosinates (for example, sodium lauroylsarcosinate) the acyl ester (for example, oleic acid ester) of isothionates and the acyl N-methyl taurides (for example, potassium N-methyl lauroyl or oleyl tauride).

Other highly preferred water soluble anionic detergent compounds are the ammonium and substituted ammonium (such as mono-, di- and triethanolamine), alkali metal (such as sodium and potassium) and alkaline earth metal (such as calcium and magnesium) salts of the higher alkyl sulfates, and the higher fatty acid monoglyceride sulfates. The particular salt will be suitably selected depending upon the particular formulation and the proportions therein.

The preferred anionic surfactants include the fluorinated higher alkyl mononuclear aromatic sulfonates, especially the higher alkyl benzene sulfonate containing 10 to 16 carton atoms in the alkyl group and the perfluoroalkylcarboxylic acids.

The last mentioned constitute the most preferred surfactants because of their unusual acid strength, chemical stability, surface activity and salt solubility characteristics. Examples of suitable perfluorocarboxylic acids include perfluoropropionic acid, perfluorobutyric acid, perfluorooctanoic acid and the like. These are available from Minnesota Mining & Manufacturing Co., St. Paul, MN. The perfluoroalkyl percarboxylic acids are used in the form of their salts as above set out and most preferably in the form of the ammonium salt. The ammonium perfluoroalkyl percarboxylate is the most preferred fluorinated anionic surfactant.

The basic inventive concept lies in the combination of the trichloroisocyanuric acid or its salt, preferably its potassium salt with the fluorinated anionic surfactant. The other components are present in order to provide the required stability and solubility.

The anti-microbial compositions of the invention are formed by admixing the trichloroisocyanuric acid in the form of its potassium salt, a fluorinated anionic surfactant, potassium monohydrogen phosphate and potassium chloride.

Preferably, the dry powder form anti-microbial compositions herein are prepared by admixing the selected ingredients in accordance with a procedure ensuring that they are dry, free-flowing powders instantly soluble in water. The procedure which has been described above comprises grinding the potassium chloride in a hammer mill to a mesh size of −100 to + 325, introducing this ground potassium chloride and potassium monohydrogen phosphate into a rotating drum mixer wherein the potassium chloride particles are coated over with the phosphate. The fluorinated organic surfactant and the trichloroisocyanuric acid ingredients are then added and the mixing completed.

The compositions of the invention are used in the form of their aqueous solutions. In areas where the 10% available chlorine limitation exists, the composition having less than 10% i.e., about 9.9% available chlorine can be dissolved in water to form a solution containing about 0.5 to about 5% or even higher of such composition. Where the limitation is not in effect, a composition containing larger amounts of active chlorine can be utilized to produce solutions having the desired content of composition for achieving the anti-microbial, disinfecting or sterilizing effect.

The compositions of the invention correspond to the following formulation:
(1) trichloroisocyanuric acid or its salt diluted by the other ingredients to a final available chlorine content of up to 9.9%–11%;
(2) potassium hydroxide in an amount sufficient to neutralize the trichloroisocyanuric acid to its potassium salt. The salt is present in an amount of 12–15%;
(3) fluorinated surfactant 0.1 to 1%;
(4) potassium monohydrogen phosphate 10%;
(5) potassium chloride up to balance 70–78%.

Compositions in accordance with the invention have been evaluated for both stability and anti-microbial activity.

A formulation as follows was prepared

| | |
|---|---|
| trichloroisocyanuric acid (potassium salt), 90% available chlorine | 12.0% |
| fluorinated surfactant (ammonium perfluoroalkyl percarboxylate) | 0.5% |
| potassium monohydrogen phosphate | 10.0% |
| potassium chloride | balance (77.5%) |

The potassium chloride had prior to use been ground in a hammer mill to a mesh size of about 200, then introduced into a rotating drum together with the potassium monohydrogen phosphate. After sufficient time had elapsed for the coating of the potassium chloride by the potassium monohydrogen phosphate to take place, the trichloroisocyanuric acid salt and fluorinated surfactant were introduced and the mixing continued.

The final product had a chlorine availability of 9.5%. A 1% solution was prepared and was effective to kill both Staph aureus and E. coli within 15 minutes at room temperature in all of the specimens where the solution was employed (10 specimens).

The same product in the form of its 2% solution killed all of the organisms in less than 5 minutes.

For establishing the compositions' cold sterilization properties, a 2% solution of the same formulation was prepared and applied to 10 specimens of air dried clostridia spores. Forty (40) hours after immersion of the specimens into the solution, ten (10) out of ten (10) or all of the specimens were killed even though the spores had been protected by fibers. The specimens had been prepared by immersing fibers into a suspension of the spores.

The preparation of the above formulation and solutions was repeated but in one instance an unfluorinated branched alkylarylsulfonate was substituted for the fluorinated surfactant. The preparations were then tested for chlorine loss. In the case of the unfluorinated branched alkylaryl sulfonate, a 37% loss of available chlorine at 120° F. was observed in nine months. In an instance where ammonium perfluoroalkyl percarboxylate was employed, the loss of available chlorine under identical conditions amounted to only 3%.

A 1% solution of the composition containing the unfluorinated surfactant lost 50% of its available chlorine in one (1) week while a 1% solution of the composition containing the fluorinated surfactant i.e., ammonium perfluoroalkyl percarboxylate lost 50% of its available chlorine in four (4) weeks.

The preparation of the above formulation was repeated but in this instance, the potassium chloride and potassium monohydrogen phosphate were introduced as taken off the shelf into the mixing drum with the other ingredients. The resultant powder form composition quickly absorbed moisture from the ambient air. The composition was noticeably moist and sticky and in this form not readily, i.e., instantly, soluble in water.

It is important in accordance with the invention that the fluorinated surfactant is physiologically acceptable.

The compositions of the invention on testing in animals in the conventional procedures have an $LD_{50}$ of 2 to 5 gms/kg (rat).

When a 3% solution of a formulation containing an ammonium perfluroalkyl percarboxylate as the fluorinated surfactant was applied topically to shaved abraded and non-abraded patches of skin in the rabbit, the solutions then allowed to air dry and then evaluated in the conventional manner for signs of irritation, no measurable irritation was observed.

What is claimed is:
1. An antimicrobial composition, in the form of a dry free flowing powder comprising
    (a) a chlorinated isocyanuric acid or its salt,
    (b) ammonium perfluoroalkylpercarboxylate, as surfactant
    (c) potassium chloride, and
    (d) potasdsium monohydrogen phosphate,
wherein the last two mentioned components are present in the form of potassium chloride particles, the preponderance of which have a mesh size of about −100 to +325 coated over with the potassium monohydrogen phosphate.

2. The antimicrobial composition of claim 1, wherein said chlorinated isocyanuric acid is 1,3,5-trichlor-s-triazine, 2,4,6-trione.

3. The antimicrobial composition of claim 1 wherein said chlorinated isocyanuric acid and said surfactant are present in a ratio of about 50:1 to 10:1 (parts by weight).

4. The antimicrobial composition of claim 1, wherein said chlorinated isocyanuric acid has about 50 to 90% available chlorine.

5. The antimicrobial composition of claim 1, wherein said chlorinated isocyanuric acid is present in the form of its potassium salt.

6. The antimicrobial composition of claim 1, wherein said composition has an active chlorine content of less than 10%.

7. The antimicrobial composition of claim 1 having the following composition:

| | |
|---|---|
| trichloroisocyanuric acid-potassium salt (90% available chlorine) | 12.0% |
| fluorinated anionic surfactant (ammonium perfluoroalkyl percarboxylate) | 0.5% |
| potassium monohydrogen phosphate | 10.0% |
| potassium chloride | balance (77.5%) |

8. The antimicrobial composition of claim 1 in the form of its aqueous solution.

9. A method for destroying microbial organisms which comprises contacting such organism with an aqueous solution containing an effective amount of an antimicrobial composition comprising
    (a) a chlorinated isocyanuric acid or its salt, (b) ammonium perfluoroalkylpercarboxylate, as surfactant
(c) potassium chloride, and
(d) potassium monohydrogen phosphate,
wherein the last two mentioned components are present in the form of potassium chloride particles, the preponderance of which have a mesh size of about $-100$ to $+325$ coated over with the potassium monohydrogen phosphate.

10. The method of claim 9 wherein said fluorinated surfactant is physiologically acceptable.

11. The method of claim 10 wherein said fluorinated surfactant has an $LD_{50}$ of 2 to 5 gms/kg determined in rats.

* * * * *